(12) United States Patent
Thomas et al.

(10) Patent No.: US 11,007,002 B2
(45) Date of Patent: May 18, 2021

(54) MANUFACTURING ELECTROSURGICAL INSTRUMENTS

(71) Applicant: GYRUS MEDICAL LIMITED, Cardiff (GB)

(72) Inventors: Daniel John Thomas, Cardiff (GB); Lewis Meurig Jones, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1134 days.

(21) Appl. No.: 14/993,408

(22) Filed: Jan. 12, 2016

(65) Prior Publication Data

US 2016/0199120 A1 Jul. 14, 2016

(30) Foreign Application Priority Data

Jan. 14, 2015 (GB) .................................. 1500532.5

(51) Int. Cl.
  *A61B 18/14* (2006.01)
  *A61B 17/00* (2006.01)
  (Continued)

(52) U.S. Cl.
  CPC ...... *A61B 18/1442* (2013.01); *A61B 18/1445* (2013.01); *A61B 18/1402* (2013.01);
  (Continued)

(58) Field of Classification Search
  CPC ......... B23P 17/04; B29C 45/00; B29C 45/17; B29C 45/40; B29C 45/12;
  (Continued)

(56) References Cited

U.S. PATENT DOCUMENTS

| | | | |
|---|---|---|---|
| 7,083,618 B2 * | 8/2006 | Couture | A61B 18/1445 606/51 |
| 7,101,372 B2 * | 9/2006 | Dycus | A61B 18/1445 606/51 |

(Continued)

FOREIGN PATENT DOCUMENTS

| | | |
|---|---|---|
| AU | 2006222705 | 10/2006 |
| CA | 2443252 A1 * | 10/2002 |

(Continued)

OTHER PUBLICATIONS

Search Report in UK Application No. GB 1500532.5, dated Jun. 5, 2015.

(Continued)

*Primary Examiner* — Carl J Arbes
(74) *Attorney, Agent, or Firm* — Oliff PLC

(57) ABSTRACT

A jaw member for an electrosurgical instrument is manufactured by providing a jaw housing (1) having a longitudinal jaw section (2), and an electrically conductive plate (11) including one or more passages (14) therein. The electrically conductive plate is disposed on the jaw section of the jaw housing, and placed into a mold (15). A flowable insulating material (18) is injected into the mold to secure the electrically conductive plate to the jaw housing, such that the flowable material (18) flows through the one or more passages (14) to form one or more stop members (21) that project a predetermined distance from the electrically conductive plate.

14 Claims, 3 Drawing Sheets

(51) Int. Cl.
    *A61B 17/29*           (2006.01)
    *A61B 18/00*           (2006.01)
    *B29L 31/00*           (2006.01)
    *B29C 45/12*           (2006.01)
    *B29C 45/14*           (2006.01)

(52) U.S. Cl.
    CPC .......... *A61B 2017/00526* (2013.01); *A61B 2017/2936* (2013.01); *A61B 2018/0063* (2013.01); *A61B 2018/00077* (2013.01); *A61B 2018/00083* (2013.01); *A61B 2018/00607* (2013.01); *A61B 2018/1455* (2013.01); *B29C 45/12* (2013.01); *B29C 45/14639* (2013.01); *B29L 2031/7546* (2013.01)

(58) Field of Classification Search
    CPC .......... B29C 45/14639; A61B 18/1402; A61B 18/1442; A61B 18/1445; A61B 2017/00526; A61B 2017/2936; A61B 2018/00077; A61B 2018/2936; A61B 2018/00607; A61B 2018/00083; A61B 2018/0063; A61B 2018/1455; B29L 2031/7546
See application file for complete search history.

(56) References Cited

U.S. PATENT DOCUMENTS

| | | | | |
|---|---|---|---|---|
| 7,150,097 | B2* | 12/2006 | Sremcich | A61B 18/1445 29/854 |
| 7,179,255 | B2* | 2/2007 | Lettice | A61B 18/148 606/32 |
| 7,267,677 | B2* | 9/2007 | Johnson | A61B 18/1445 606/171 |
| 7,473,253 | B2 | 1/2009 | Dycus et al. | |
| 7,582,087 | B2* | 9/2009 | Tetzlaff | A61B 18/1442 606/51 |
| 7,877,852 | B2 | 2/2011 | Unger et al. | |
| 7,922,953 | B2 | 4/2011 | Guerra | |
| 7,931,649 | B2* | 4/2011 | Couture | A61B 18/1445 606/45 |
| 8,112,871 | B2* | 2/2012 | Brandt | A61B 18/1445 29/592.1 |
| 8,241,284 | B2 | 8/2012 | Dycus et al. | |
| 8,266,783 | B2* | 9/2012 | Brandt | A61B 18/1442 29/527.1 |
| 8,439,913 | B2* | 5/2013 | Horner | H01L 41/25 606/52 |
| 8,814,864 | B2* | 8/2014 | Gilbert | A61B 18/1442 606/51 |
| 9,750,561 | B2* | 9/2017 | Brandt | A61B 18/1445 |
| 2003/0014053 | A1 | 1/2003 | Nguyen et al. | |
| 2004/0122423 | A1* | 6/2004 | Dycus | A61B 90/03 606/51 |
| 2005/0021025 | A1* | 1/2005 | Buysse | A61B 18/1442 606/51 |
| 2005/0113828 | A1* | 5/2005 | Shields | A61B 18/1442 606/51 |
| 2006/0167452 | A1* | 7/2006 | Moses | A61B 17/3201 606/51 |
| 2007/0074807 | A1* | 4/2007 | Guerra | A61B 18/1445 156/242 |
| 2007/0265616 | A1 | 11/2007 | Couture et al. | |
| 2008/0015575 | A1 | 1/2008 | Odom et al. | |
| 2008/0195093 | A1* | 8/2008 | Couture | A61B 18/1445 606/45 |
| 2009/0082767 | A1* | 3/2009 | Unger | A61B 18/1445 606/51 |
| 2009/0082769 | A1* | 3/2009 | Unger | A61B 18/1445 606/52 |
| 2009/0204114 | A1* | 8/2009 | Odom | A61B 18/1206 606/51 |
| 2009/0254081 | A1* | 10/2009 | Allison | A61B 18/1442 606/39 |
| 2011/0072638 | A1* | 3/2011 | Brandt | A61B 18/1442 29/527.1 |
| 2011/0073246 | A1* | 3/2011 | Brandt | A61B 18/1445 156/242 |
| 2012/0083783 | A1 | 4/2012 | Davison et al. | |
| 2012/0265241 | A1 | 10/2012 | Hart et al. | |
| 2013/0085496 | A1 | 4/2013 | Unger et al. | |
| 2013/0185922 | A1* | 7/2013 | Twomey | A61B 18/1445 29/527.1 |
| 2013/0226177 | A1 | 8/2013 | Brandt et al. | |
| 2013/0255063 | A1* | 10/2013 | Hart | A61B 18/085 29/505 |
| 2014/0025073 | A1 | 1/2014 | Twomey et al. | |
| 2014/0194875 | A1 | 7/2014 | Reschke et al. | |
| 2015/0018816 | A1 | 1/2015 | Latimer | |

FOREIGN PATENT DOCUMENTS

| | | |
|---|---|---|
| CN | 101683282 A | 3/2010 |
| CN | 103211647 A | 7/2013 |
| EP | 1486177 | 12/2004 |
| EP | 1795140 | 6/2007 |
| EP | 2425791 | 3/2012 |
| EP | 2 687 176 A1 * | 1/2014 |
| EP | 2687176 | 1/2014 |
| EP | 2687176 A1 | 1/2014 |
| JP | 2008-212663 A | 9/2008 |
| JP | 2011-146350 A | 7/2011 |
| WO | 2015/197395 A1 | 12/2015 |

OTHER PUBLICATIONS

Nov. 2, 2018 Office Action issued in Chinese Patent Application No. 201610042020.4.
U.S. Appl. No. 14/992,137, filed Jan. 11, 2016, Thomas, et al.
U.S. Appl. No. 14/992,193, filed Jan. 11, 2016, Thomas, et al.
U.S. Appl. No. 14/993,496, filed Jan. 12, 2016, Thomas, et al.
U.S. Appl. No. 14/994,464, filed Jan. 13, 2016, Jones.
Sep. 24, 2019 Office Action issued in Japanese Patent Application No. 2016-00656.
Jun. 9, 2020 Office Action issued in Japanese Patent Application No. 2016-004656.

* cited by examiner

MANUFACTURING ELECTROSURGICAL INSTRUMENTS

This application claims priority to United Kingdom Application No. 1500532.5 filed 14 Jan. 2015 the entire contents of which is incorporated herein by reference.

TECHNICAL FIELD

Embodiments of the invention relate to a method for manufacturing a jaw member for an electrosurgical instrument, particularly a forceps instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to manufacture jaw members for electrosurgical instruments by an overmoulding process, in which components are assembled into a mould and flowable material is introduced into the mould to surround the components and form the completed jaw member. U.S. Pat. Nos. 7,150,097 & 7,922,953 are examples of such manufacturing methods. It is also known to provide stop members on the jaw member, and U.S. Pat. No. 7,877,852 is one example of such a manufacturing method.

SUMMARY OF THE INVENTION

Embodiments of the present invention attempt to provide an improved alternative to manufacturing methods such as those described above.

Accordingly, a method for manufacturing a jaw member for an electrosurgical instrument, comprises the steps of:

providing a jaw housing having a longitudinal jaw section;

providing an electrically conductive plate including one or more passages therethrough;

disposing the electrically conductive plate on the jaw section of the jaw housing;

placing the jaw housing and the electrically conductive plate into a mould;

injecting a flowable insulating material into the mould to secure the electrically conductive plate to the jaw housing, such that the flowable material flows through the one or more passages to form one or more stop members that project a predetermined distance from the electrically conductive plate;

allowing the flowable insulating material to solidify; and removing the jaw housing, electrically conductive plate and the solidified insulating material from the mould as a jaw member.

In U.S. Pat. No. 7,877,852 referred to above, the stop members are preformed in a separate insulating housing which is then assembled together with a conductive sealing plate having apertures therein, the stop members of the insulating housing protruding through the apertures. In an alternative arrangement, the stop members are dispersed in molten form into cavities formed in the sealing plate, and solidify to form the stop members. Embodiments of the present invention provide an improved alternative to either of these arrangements, in which the one or more stop members are formed during the overmoulding process, with flowable material flowing up through passages formed in the conductive plate. In this way, the one or more stop members are part of the overmoulded component as opposed to a preformed component such as a housing which needs to be carefully assembled together with the other components.

Preferably, the injecting step is such that the predetermined distance is about 20 μm to about 350 μm (0.00079 inches to about 0.014 inches). By ensuring that the one or more stop members project from the electrically conductive plate by this sort of distance, effective sealing of tissue grasped between the jaw members is achieved.

The method conveniently includes the step of providing a pre-moulded insert that can be received within the jaw housing. The step of disposing the electrically conductive plate on the jaw section of the jaw housing conveniently comprises inserting the pre-moulded insert into the jaw housing, and then placing the electrically conductive plate on to the insert. Conveniently, the method includes the additional step of disposing an electrically conductive lead against the conductive plate before the flowable insulating material is injected into the mould. In this way, the pre-moulded insert acts as a base for the electrically conductive plate and as a locator for the lead prior to and during the subsequent overmoulding process. The flowable insulating material preferably then secures the lead in electrical connection with the conductive plate.

The mould is preferably such that the solidified insulating material around the one or more stop members does not overlap the conductive plate. This ensures that no insulating material obscures the sealing surface of the electrically conductive plate. 14. For example, the mould comprises volumes located above the one or more passages when the jaw housing and plate are located in the mould, the volumes permitting the flowable insulating material to flow thereinto to form the stop members. In one embodiment the mould abuts against the electrically conductive plate when the plate is placed into the mould in regions other than where the volumes are provided whereby to prevent the flowable insulating material from encroaching onto an upper surface of the electrically conductive plate.

The electrically conductive plate preferably includes a longitudinally extending slot capable of receiving a translatable knife blade. In this way, the sealing instrument can also be used to sever tissue after it has been sealed by the jaw members.

The conductive plate preferably includes a plurality of passages, such that a plurality of stop members is formed during the overmoulding process. Typically, the passages are disposed along the longitudinal axis of the conductive plate. According to one convenient arrangement, the passages are disposed adjacent the longitudinally extending slot, typically disposed either side of the longitudinally extending slot. The one or more passages are conveniently through holes formed in the conductive plate, or conceivably cut-outs formed in the conductive plate, either adjacent the edge of the plate or adjacent the longitudinally extending slot, should one be provided. Whatever type of passage or passages are employed, they provide a complete communication through the conductive plate from one side to the other, such that flowable material can permeate the conductive plate in order to form the one or more stop members.

An embodiment of the invention further resides in a method for manufacturing an end effector assembly for sealing tissue, comprising the steps of:

providing a pair of first and second jaw housings each having a longitudinal jaw section, and a pair of electrically conductive plates, at least one of the electrically conductive plates including one or more passages therein;

disposing the electrically conductive plates on the jaw sections of the jaw housing;

placing the jaw housings and the electrically conductive plates into moulds;

injecting a flowable insulating material into the moulds to secure the electrically conductive plates to the jaw housings, such that the flowable material flows through the one or more passages to form one or more stop members that project a predetermined distance from the electrically conductive plate;

allowing the flowable insulating material to solidify;

removing the jaw housings, electrically conductive plates and the solidified insulating material from the moulds to form two jaw members; and assembling the jaw members about a pivot such that the electrically conductive plates are substantially opposed to each other in pivotal relation relative to one another.

The injecting step is preferably such that the predetermined distance is about 25 μm to about 350 μm (0.001 inches to about 0.014 inches).

An embodiment of the invention also resides in a jaw member or an end effector for an electrosurgical instrument made in accordance with the methods as previously described.

DESCRIPTION OF THE DRAWINGS

Embodiments of the invention will now be further described, by way of example only, with reference to the accompanying drawings, in which.

DESCRIPTION OF THE EMBODIMENTS

Figure 1:
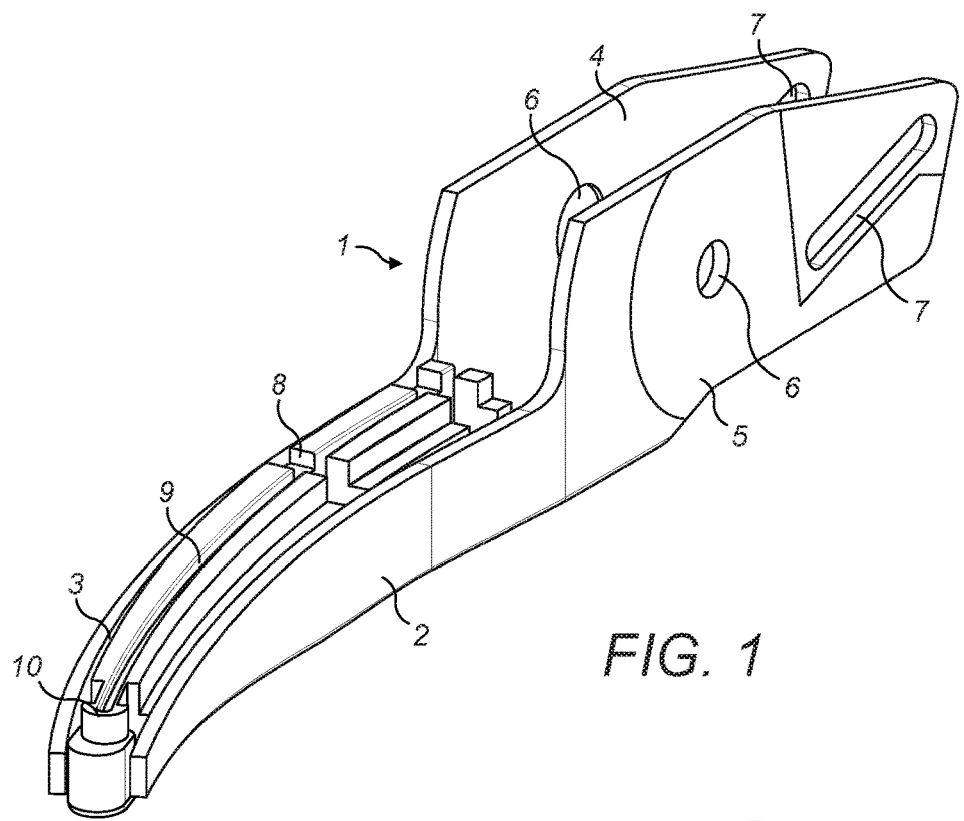
FIG. 1 is a schematic view of a jaw component during a first stage of a manufacturing method in accordance with an embodiment of the present invention.

Referring to FIG. 1, a metallic jaw frame 1 is manufactured either from stamping, machining or by a casting process, and comprises an elongate jaw body 2 with a generally U-shaped cross section defining a cavity 3 therein. Proximal of the jaw body 2 is a pair of flanges 4 & 5, each having a pivot aperture 6 and an angled cam slot 7. A preformed insert 8 of moulded plastics material is placed inside the cavity 3 of the jaw body 2, the insert 8 having a raised longitudinal portion 9 defining a slot 10 therein.

Figure 2:
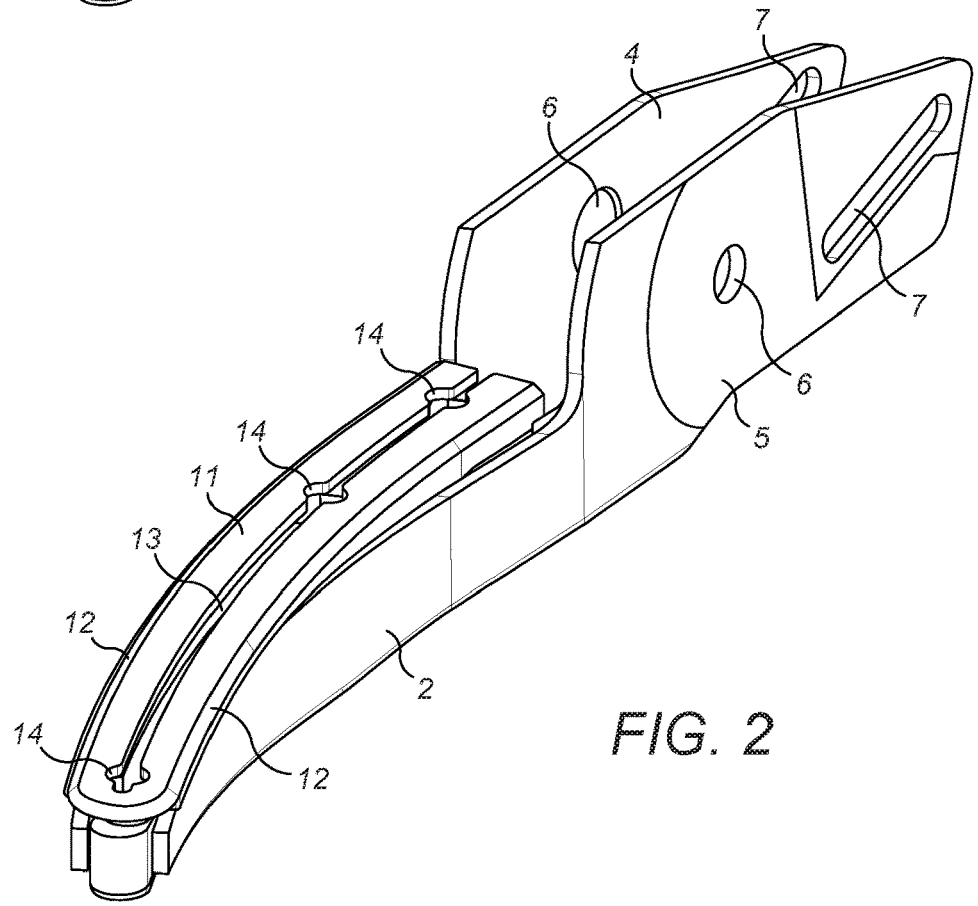
FIG. 2 is a schematic view of a jaw component during a subsequent stage of a manufacturing method in accordance with the embodiment of the present invention.

After the insert 8 has been placed inside the jaw frame 1, the next step is for a conductive shim 11 to be placed on top of the insert 8, the shim having downturned edges 12 and a longitudinal slot 13 aligned with the slot 10 in the insert 8. The location of the shim 11 is shown in FIG. 2. An electrical lead (not shown) can be located on the shim 11 at the proximal end thereof in order to provide a supply of electric current to the shim in order for it to act as an electrode during use. The shim 11 includes a plurality of cut-outs 14, longitudinally spaced along the shim and located either side of the slot 13.

Figure 3:
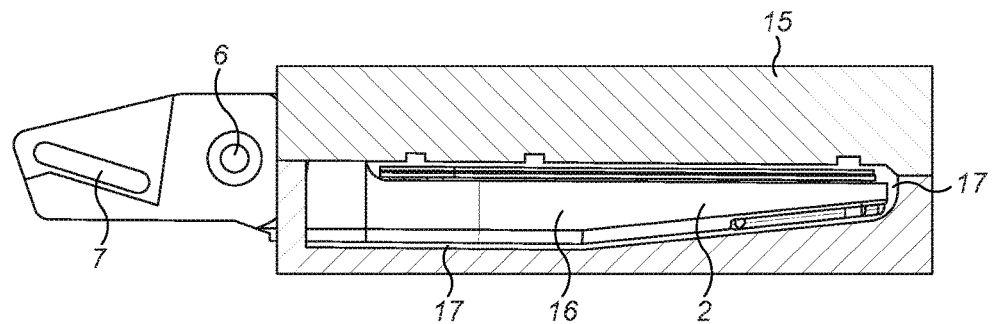
FIG. 3 is a sectional side view of a jaw component during a further stage of a manufacturing method in accordance with the embodiment of the present invention.
Figure 4:
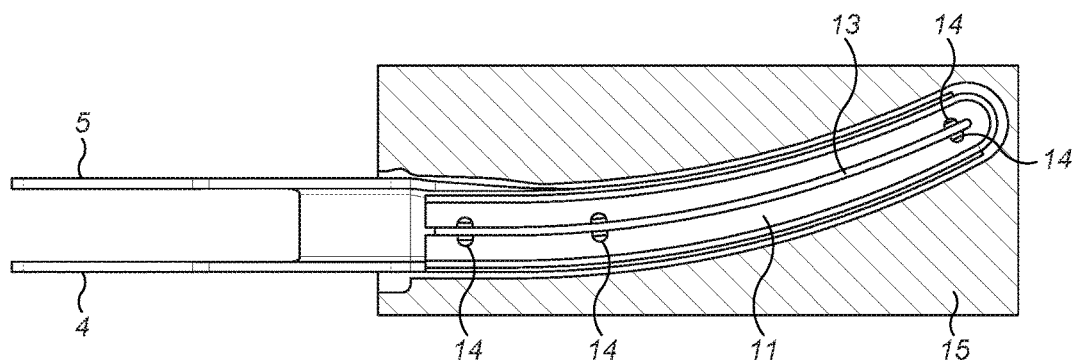
FIG. 4 is a sectional plan view of a jaw component during the manufacturing stage of FIG. 3.
Figure 5:
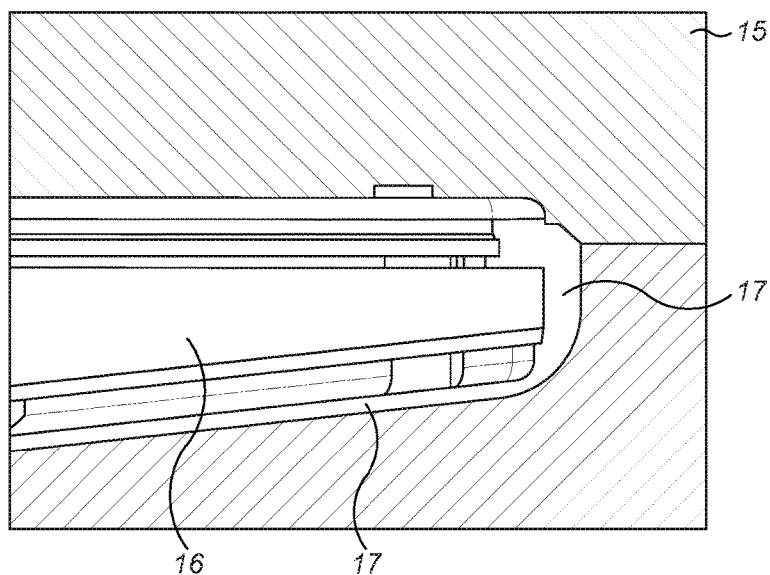
FIG. 5 is an enlarged sectional view of a portion of FIG. 3.

Once the insert 8 and shim 11 have been added to the jaw frame 1, the next step is to place the jaw frame into a mould 15, as shown in FIGS. 3 to 5. The mould 15 has a cavity 16 into which the jaw frame is accommodated, the cavity being of such a shape and size as to leave a space 17 surrounding the jaw frame. Once the jaw frame is located within the mould 15, a flowable plastics material 18 such as polypropylene is injected into the mould, so as to fill any available areas, including the space 17. The plastics material 18 flows into the cavity 3 in the jaw body, and between the jaw body 2 and the insert 8. The material 18 also flows from the cavity 3 up though the cut-outs 14, to protrude above the shim 11.

Figure 6:
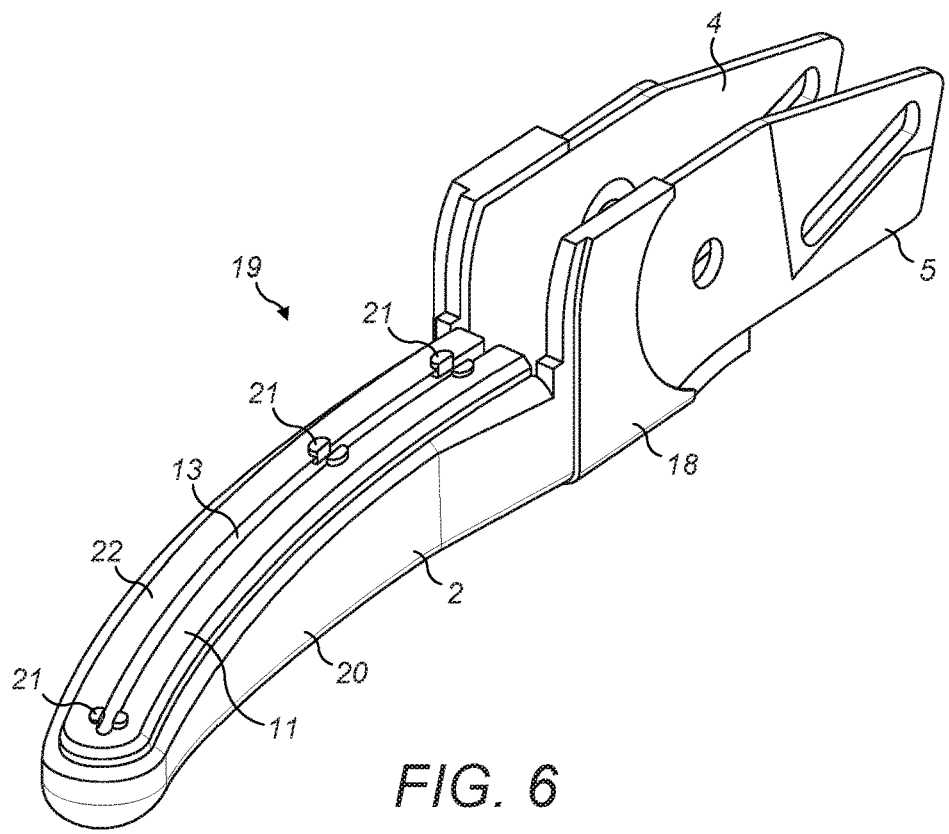
FIG. 6 is a schematic diagram of a jaw component during a final stage of a manufacturing method in accordance with the embodiment of the present invention.
Figure 7:
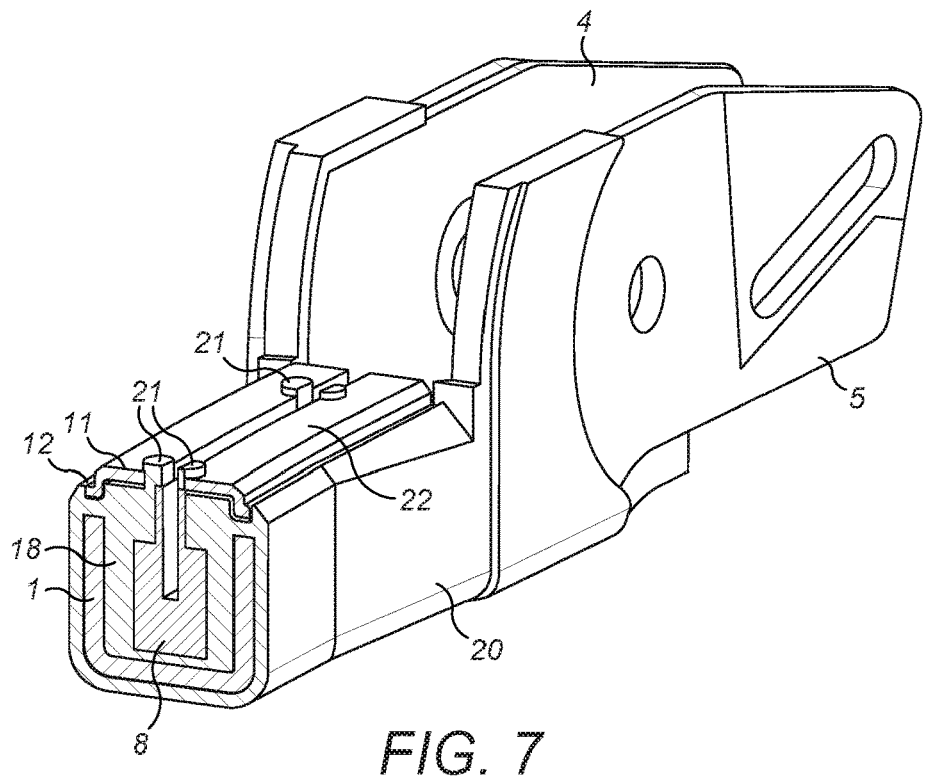
FIG. 7 is a schematic sectional view of FIG. 6.

The flowable material 18 is allowed to harden, and the mould 15 is then opened to allow the jaw frame to be removed therefrom. The hardened material 18 now binds together the jaw frame 1, the insert 8 and the shim 11 into a completed jaw member 19, and forms an outer covering 20 around the jaw member 19. The material 18 also forms stop members 21 protruding above the shim 11, as shown in FIGS. 6 & 7.

The mould 15 is such that the flowable material 18 does not encroach onto the upper surface 22 of the shim 11 so as to maintain it as a tissue contacting surface. The jaw member 19 can be assembled together with another similar jaw member to form an end effector for a forceps instrument, as will be known in the art for the sealing and/or cutting of tissue. The jaw member 19 can be mounted on a pivot pin (not shown) passing through the pivot apertures 6, and a cam pin (also not shown) can be located in the cam slots 7 in order to cause the pivoting of one jaw with respect to the other between open and closed positions.

Those skilled in the art will appreciate that modifications to the above can be made without departing from the scope of the present invention, and that alternative configurations of components can be employed. By providing cut-outs or through holes for the flowable material to rise up above the shim 11, stop members can be formed during the overmoulding process, rather than needing to be pre-formed in advance of the overmoulding, or added subsequently by an additional method step or steps.

The invention claimed is:

1. A method for manufacturing a jaw member for an electrosurgical instrument, comprising the steps of:
   providing a jaw housing having a longitudinal jaw section;
   providing an electrically conductive plate including one or more passages that extend through a thickness direction of the electrically conductive plate;
   disposing the electrically conductive plate on the jaw section of the jaw housing;
   placing the jaw housing and the electrically conductive plate into a mould;
   injecting a flowable insulating material into the mould to secure the electrically conductive plate to the jaw housing, such that the flowable material flows through the one or more passages to form one or more stop members that project a predetermined distance from the electrically conductive plate;
   allowing the flowable insulating material to solidify; and
   removing the jaw housing, electrically conductive plate and the solidified insulating material from the mould as a jaw member,
   wherein the mould comprises volumes located above the one or more passages when the jaw housing and plate are located in the mould, the volumes permitting the flowable insulating material to flow thereinto to form the stop members.

2. A method according to claim 1, wherein the injecting step is such that the predetermined distance is about 20 μu to about 350 μm (0.00079 inches to about 0.014 inches).

3. A method according to claim 1, including the step of providing a pre-moulded insert that can be received within the jaw housing.

4. A method according to claim 3, wherein the step of disposing the electrically conductive plate on the jaw section of the jaw housing comprises inserting the pre-moulded insert into the jaw housing, and then placing the electrically conductive plate on to the insert.

5. A method according to claim 1, including the additional step of disposing an electrically conductive lead against the conductive plate before the flowable insulating material is injected into the mould.

6. A method according to claim 5, wherein the flowable insulating material secures the lead in electrical connection with the conductive plate.

7. A method according to claim 1, wherein the conductive plate includes a plurality of passages therethrough.

8. A method according to claim 7, wherein the plurality of passages are disposed along the longitudinal axis of the conductive plate.

9. A method according to claim 1, wherein the one or more passages are through holes.

10. A method according to claim 1, wherein the one or more passages are cut-outs.

11. A method according to claim 1, wherein the mould abuts against the electrically conductive plate when the plate is placed into the mould in regions other than where the volumes are provided whereby to prevent the flowable insulating material from encroaching onto an upper surface of the electrically conductive plate.

12. A method for manufacturing a jaw member for an electrosurgical instrument, comprising the steps of:
    providing a jaw housing having a longitudinal jaw section;
    providing an electrically conductive plate including one or more passages that extend through a thickness direction of the electrically conductive plate;
    disposing the electrically conductive plate on the jaw section of the jaw housing;
    placing the jaw housing and the electrically conductive plate into a mould;
    injecting a flowable insulating material into the mould to secure the electrically conductive plate to the jaw housing, such that the flowable material flows through the one or more passages to form one or more stop members that project a predetermined distance from the electrically conductive plate;
    allowing the flowable insulating material to solidify; and
    removing the jaw housing, electrically conductive plate and the solidified insulating material from the mould as a jaw member, wherein:
    the electrically conductive plate includes a longitudinally extending slot configured to receive a translatable knife blade;
    the passages are disposed adjacent the longitudinally extending slot; and
    the mould comprises volumes located above the one or more passages when the jaw housing and plate are located in the mould, the volumes permitting the flowable insulating material to flow thereinto to form the stop members.

13. A method according to claim 12, wherein the passages contact either side of the longitudinally extending slot.

14. A jaw member for an electrosurgical instrument manufactured by the following steps:
    i) providing a jaw housing having a longitudinal jaw section;
    ii) providing an electrically conductive plate including one or more passages that extend through a thickness direction of the electrically conductive plate;
    iii) disposing the electrically conductive plate on the jaw section of the jaw housing;
    iv) placing the jaw housing and the electrically conductive plate into a mould;
    v) injecting a flowable insulating material into the mould to secure the electrically conductive plate to the jaw housing, such that the flowable material flows through the one or more passages to form one or more stop members that project a predetermined distance from the electrically conductive plate;
    vi) allowing the flowable insulating material to solidify; and
    vii) removing the jaw housing, electrically conductive plate and the solidified insulating material from the mould as a jaw member,
    wherein the mould comprises volumes located above the one or more passages when the jaw housing and plate are located in the mould, the volumes permitting the flowable insulating material to flow thereinto to form the stop members.

* * * * *